(12) United States Patent
Ayral-Kaloustian et al.

(10) Patent No.: US 6,403,581 B1
(45) Date of Patent: Jun. 11, 2002

(54) METHOD OF INHIBITION OF FARNESYL-PROTEIN TRANSFERASE USING SUBSTITUTED BENZ (CD) INDOL-2-IMINE AND-AMINE DERIVATIVES

(75) Inventors: Semiramis Ayral-Kaloustian, Tarrytown; Douglas Bruce Kitchen, Schenectady, both of NY (US); Andrei Shavnya, East Lyme, CT (US)

(73) Assignee: American Cyanamid Company, Madison, NJ (US)

(*) Notice: Subject to any disclaimer, the term of this patent is extended or adjusted under 35 U.S.C. 154(b) by 0 days.

(21) Appl. No.: 09/765,911

(22) Filed: Jan. 19, 2001

Related U.S. Application Data
(60) Provisional application No. 60/266,306, filed on Jan. 19, 2000.

(51) Int. Cl.[7] ............................................. A61K 31/535
(52) U.S. Cl. .................... 514/232.8; 514/318; 514/323; 514/333; 514/339; 514/394; 514/397; 514/411
(58) Field of Search ............................. 514/232.8, 318, 514/323, 333, 339, 394, 397, 411

(56) References Cited

U.S. PATENT DOCUMENTS

| | | |
|---|---|---|
| 3,649,645 A | 3/1972 | Yamada et al. |
| 3,959,310 A | 5/1976 | Brack et al. |
| 4,146,541 A | 3/1979 | Schwander et al. |
| 4,201,713 A | 5/1980 | Harnisch |
| 4,261,896 A | 4/1981 | Tomcufcik et al. |
| 4,728,663 A | 3/1988 | Tomcufcik et al. |
| 5,079,247 A | 1/1992 | Tomcufcik et al. |
| 5,081,131 A | 1/1992 | Tomcufcik et al. |
| 5,229,411 A | 7/1993 | Newman et al. |
| 6,306,874 B1 * | 10/2001 | Fraley et al. ................ 514/300 |

OTHER PUBLICATIONS

Pharmaprojects, 1988, No. 5128; R–115777, Pharmaprojects 1998, No. 5532.
T. M. Williams, Exp. Opin. Ther. Patents, 1998, 8, 553.
H. W. Park, S.R. Boduluri, J.F. Moomaw, P.J. Casey and L.S. Beese, Science, 1997, 275, 1800.
S.P. Fricker and R.G. Buckley, Anticancer Reasearch, 1996, 16, 3755–3760.
S. Ayral–Kaloustian and J.S Skotnicki, Annu. Rep. Med. Chem., 1996, 31, 165, and references therein).
Michael R. Boyd and Kenneth D. Paull, Drug Development Research 34, 91–109 (1995).
G.L. Bolton, J.S. Sebolt–Leopold and J.C. Hodges, Annu. Rep. Med. Chem. 1994, 29, 165.
R.J. A. Grand in "New Molecular Targets in Cancer Chemotherapy" J. D. Kerr, and P. Workman, Eds., CR Press, Boca Raton, FL, 1994, p. 97.
James, G.L. Brown, M.S., and Goldstein, J.L., Methods in Enzymology, 1995, 225, 38–46.
Ana Maria Garcia, Cheryl Rowell, Karen Ackermann, James J. Kowalczyk and Michael D. Lewis, the Journal of Biological Chemistry vol. 268, No. 25 Issue of Sep. 5, pp. 18415–18418, 1993.
Moomaw, J. F. Casey, P.J., J. Biol. Chem., 1992, 267, 17438–17443.
A. Monks Et. Al, J. Natl. Cancer Inst. IT., 1991, 83, 757–66.
L. V. Rubinstein, R.H. Shoemaker, K.D.Paull, R.M. Simon, S Tosini, P. Skehan, D .A. Scudiero, A. Monks, and M.R. Boyd, J. Natl. Cancer Instit, 1990, 82 (13), 1113–1118.
P. Skehan, R. Storeng, D Scudiero, A. Monks, J. McMohan, D. Vistica, J. Warren, H. Bokesh, S. Kenney and M.R. Boyd, J. Natl. Cancer Instit, 1990, 82 (13), 1107–1112.
J.F. Hancock, H. Paterson, and C.J. Marshall, Cell, 1990, 63, 133.
P. J. Casey, P.A. Solski, C.J. Der, and J.E. Buss, Proc. Natl, Acad. Sci. USA., 1989, 86, 8323.
J.L. Bos. Cancer Res., 1989, 49, 4682.

* cited by examiner

Primary Examiner—James H. Reamer
(74) Attorney, Agent, or Firm—Daniel B. Moran

(57) ABSTRACT

The invention is a method of treating, inhibiting or controlling a ras-associated disease by inhibiting farnesyl-protein transferase(FPTase) enzyme, treating ras oncogene-dependent tumors, which include cancers of pancreas, breast, lung, colon, epidermis, prostate, bladder, thyroid, myelodysplastic tumors and myeloid leukemia; controlling metastasis, suppressing angiogenesis, inducing apoptosis, and in treating Ras-associated proliferative diseases other than cancer, such as restenosis, neuro-fibromatosis, endometriosis, and psoriasis, in a mammal in need thereof, which comprises administering to said mammal an effective amount of a compound of Formula I:

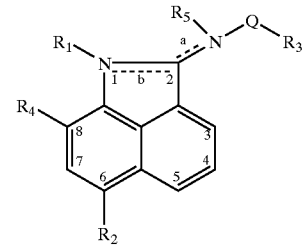

Formula I or a pharmaceutically acceptable salt thereof, wherein $R_1$, $R_2$, $R_3$, $R_4$, $R_5$, Q, a, and b are defined in the specification.

12 Claims, No Drawings

METHOD OF INHIBITION OF FARNESYL-PROTEIN TRANSFERASE USING SUBSTITUTED BENZ (CD) INDOL-2-IMINE AND-AMINE DERIVATIVES

CROSS REFERENCE TO RELATED APPLICATIONS

This application claims benefit of U.S. Provisional Application No. 60/266,306 which was converted from U.S. patent application Ser. No. 09/487,517, filed Jan. 19, 2000 pursuant to a petition filed under 37 C.F.R. 1.53 (c) (2) filed Apr. 12, 2000.

BACKGROUND OF THE INVENTION a) Field of the Invention

The present invention provides a method of treating or controlling ras oncogene-dependent tumors and associated proliferative diseases in a mammal in need thereof by inhibition of farnesyl-protein transferase(FPTase) which comprises administering to said mammal an effective amount of a substituted benz[cd]indol-2-imine and -amine derivatives and pharmaceutically acceptable salts thereof.

These compounds may also inhibit other prenyl modifications of proteins.

b) Description of the Prior Art

Mammalian H-, K-, and N-Ras proteins, encoded by H-, K-, and N-ras proto-oncogenes, respectively, are 21 kD GTP-binding proteins which possess intrinsic GTPase activity and play a fundamental role in cell proliferation and differentiation (G. L. Bolton, J. S. Sebolt-Leopold, and J. C. Hodges, *Annu. Rep. Med. Chem.*, 1994, 29, 165; R. J. A. Grand in "New Molecular Targets in Cancer Chemotherapy" J. D. Kerr, and P. Workman, Eds., *CRC Press*, Boca Raton, Fla., 1994, p. 97). Specific mutations in the ras gene impair GTPase activity of Ras, leading to uninterrupted growth signals and to the transformation of normal cells into malignant phenotypes. Mutant ras oncogenes are found in approximately 25% of all human cancers, including 90% of pancreatic, 50% of colon, and 50% of thyroid tumors (J. L. Bos, *Cancer Res.*, 1989, 49, 4682). It has been shown that normal cells transfected with mutant ras gene become cancerous and that unfarnesylated, cytosolic mutant Ras protein does not anchor in cell membranes and cannot induce this transformation (J. F. Hancock, H. Paterson, and C. J. Marshall, *Cell*, 1990, 63, 133). Posttranslational modification and plasma membrane association of mutant Ras is essential for this transforming activity. The first and required step in the processing of Ras is farnesylation at the cysteine residue of its carboxyl terminal motif, CAAX (C=Cys-186, A=aliphatic amino acid, X=usually methionine, serine or glutamine). Since its identification, the enzyme farnesyl-protein transferase (FPTase) that catalyzes this first processing step has emerged as a promising target for therapeutic intervention (H.-W. Park, S. R. Boduluri, J. F. Moomaw, P. J. Casey, and L. S. Beese, *Science*, 1997, 275, 1800; P. J. Casey, P. A. Solski, C. J. Der, and J. E. Buss, *Proc. Natl. Acad. Sci. U.S.A.*, 1989, 86, 8323; S. Ayral-Kaloustian and J. S. Skotnicki, *Annu. Rep. Med. Chem.*, 1996, 31, 165, and references therein). Major milestones have been achieved with small molecules, such as mimics of the tetrapeptide CAAX and analogs of farnesyl pyrophosphate, that show efficacy without toxicity in vitro as well as in mouse models bearing ras-dependent tumors or human xenografts with H-, N-, or K-ras mutations (S. Ayral-Kaloustian and J. S. Skotnicki, *Annu. Rep. Med. Chem.*, 1996, 31, 165, and references therein; T. M. Williams, *Exp. Opin. Ther. Patents*, 1998, 8, 553, and references therein). Several low-molecular weight compounds that inhibit FPTase have entered Phase I trials in humans (SCH-66336, *Pharmaprojects*, 1998, No. 5128; R-115777, *Pharmaprojects*, 1998, No. 5532).

Accordingly, there is still a need for drugs for treating and preventing cancer. In particular, there is a need for drugs which inhibit or treat the growth of tumors expressing an activated Ras oncogene and which include cancers of the pancreas, colon, bladder and thyroid.

The present invention accordingly provides a method of treating Ras-associated proliferative diseases including cancer, or in the treatment of diseases associated with other prenyl modifications of proteins.

SUMMARY OF THE INVENTION

This invention provides a method of treating, inhibiting or controlling a ras-associated disease by inhibiting farnesyl-protein transferase enzyme in a mammal in need thereof, which comprises administering to said mammal an effective amount of a compound of Formula I:

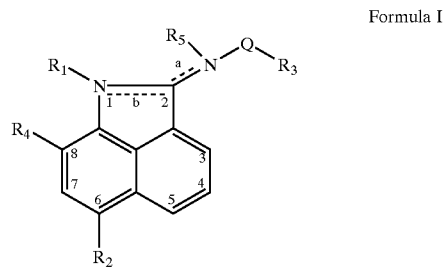

Formula I wherein:
the dotted line ------ at position a is an optional additional bond;
the dotted line ------ at position b is an optional additional bond;
$R_1$ is selected from the group consisting of H, alkyl of 1 to 6 carbon atoms, phenyl, and a moiety of the following:

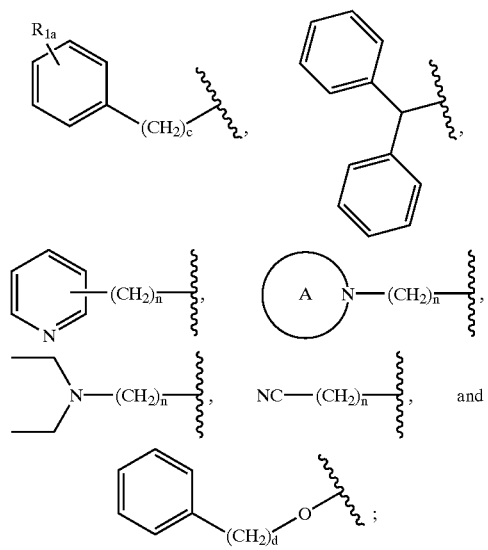

$R_2$ is selected from alkoxy of 1 to 8 carbon atoms, trifluoromethyl and halogen;

c is an integer of 0 to 3;
d is an integer of 1 to 3;
n is an integer of 1 to 6;
A is a monocyclic ring having 5 or 6 ring atoms optionally having saturated or unsaturated bonds and containing 1 or 2 nitrogen atoms and 0 or 1 oxygen atoms;

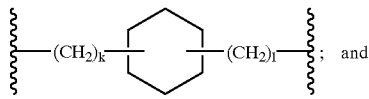

R$_2$ is selected from the group consisting of hydrogen, alkoxy of 1 to 8 carbon atoms, alkylthio of 1 to 8 carbon atoms, alkylsulfonyl of 1 to 8 carbon atoms, arylsulfonyl of 6 to 12 carbon atoms, hydroxy, hydroxyalkyl of 1 to 8 carbon atoms, mercapto, alkylcarbonyloxy of 1 to 8 carbon atoms, amino, mono(alkyl)amino of 1 to 8 carbon atoms, di(alkyl)amino of 1 to 16 carbon atoms, (alpha, omega-alkylene)amino of 2 to 8 carbon atoms, alkyl of 1 to 8 carbon atoms, arylalkyl of 7 to 20 carbon atoms, cycloalkyl of 3 to 10 carbon atoms, cycloalkylalkoxy of 3 to 10 carbon atoms, alkylcarbonyl of 1 to 8 carbon atoms, arylcarbonyl of 6 to 12 carbon atoms, cyano, sulfonamido, N-alkylsulfonamido of 1 to 8 carbon atoms, N,N-(dialkyl)sulfonamido of 2 to 16 carbon atoms, alpha-hydroxyalkyl of 1 to 8 carbon atoms, alpha-aminoalkyl of 1 to 8 carbon atoms, alpha-alkylaminoalkyl of 2 to 16 carbon atoms, alpha-(dialkyl)amino(alkyl) of 3 to 24 carbon atoms, carboxamido, N-(alkyl)carboxamido of 1 to 8 carbon atoms, N,N-(dialkyl)carboxamido of 2 to 16 carbon atoms, and halogen;
Q is selected from
a) a chain —(CH$_2$)$_m$— optionally containing one or more —CH=CH— or —C≡C— linkages and further optionally replacing one of the chain —CH$_2$— groups with —O—, —S—, —SO$_2$—, —NH—, —N-alkyl of 1 to 8 carbon atoms, —N-aryl of 6 to 12 carbon atoms, or —(C=O)NH— and further optionally substituting said chain with substitutents selected from alkyl of 1 to 8 carbon atoms, cycloalkyl of 3 to 10 carbon atoms, arylalkyl of 7 to 20 carbon atoms, aryl of 6 to 12 carbon atoms, hydroxy, alkoxy of 1 to 8 carbon atoms, and fluoro; or
b) a moiety of the formula

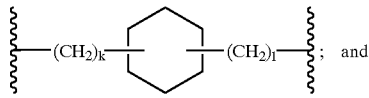

c) a moiety of the formula

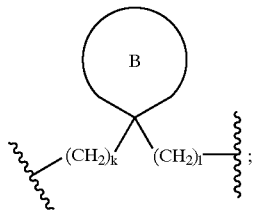

k, l and m are independently selected from an integer of 1 to 12;

B is a monocyclic cycloalkyl ring having 3 to 10 ring atoms;
R$_3$ is selected from hydrogen, and a substituted or unsubstituted heterocycle;
R$_4$ is selected from hydrogen, halogen, and alkyl of 1 to 6 carbon atoms;
R$_5$ is selected from hydrogen and alkyl of 1 to 8 carbon atoms;
R$_5$ and Q taken together with the nitrogen atom to which they are attached form a monocyclic ring having the moiety

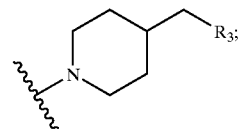

provided that at either position a or b is present an additional bond and if at b, is present an additional bond, R$_1$ is not present and a is not present, and if at a, is present an additional bond, R$_5$ is not present and b is not present;
or a pharmaceutically acceptable salt thereof.

For the compounds defined above and referred to herein, unless otherwise noted, the following terms are defined. The term halogen may be selected from fluorine, chlorine, bromine, and iodine.

The term alkyl means a branched or branched saturated or unsaturated hydrocarbon radical of 1 to 8 carbon atoms optionally containing double or triple bonds. Examples of alkyl radicals include methyl, ethyl, propyl, isopropyl, butyl, t-butyl, neopentyl, pentyl, heptyl, butenyl, pentyl, butynyl and pentynyl and the like unless otherwise specified.

Alkylthio as used here means an alkyl-S— in which the alkyl group is as previously described. Thioalkyl groups include thiomethyl and the like.

Mono(alkyl)amino is defined as a nitrogen atom substituted with alkyl of 1 to 8 carbon atoms.

Di(alkyl)amino is defined as a nitrogen atom independently substituted with two alkyl groups of 1 to 8 carbon atoms.

Alkylsulfonyl as used herein refers to the radical —SO$_2$ alkyl where alkyl is previously defined.

The term alkoxy means a branched or unbranched hydrocarbon radical of 1 to 8 carbon atoms attached through an oxygen bridge and including for example, methoxy, ethoxy, propoxy, pentoxy and the like.

The term cycloalkyl means an unsubstituted or substituted saturated or unsaturated monocyclic ring of 3 to 10 carbon atoms which include cyclopropane, cyclobutane, cyclopentane, cyclohexane, cyclobutenyl, cyclopentyl, cyclobutynyl, cyclopentynyl and the like, preferred substituents are selected from the group consisting of hydrogen, halogen, trifluoromethyl, cyano, carboxy, amino, alkyl of 1 to 8 carbon atoms, benzylamino, allylamino, alkylamino of 1 to 8 carbon atoms, dialkylamino of 1 to 8 carbon atoms in each alkyl group, alkylthio of 1 to 8 carbon atoms, alkylsulfonyl of 1 to 8 carbon atoms, acetyl, acetamido, phenyl and benzoyl.

The term alkylene means a hydrocarbon radical of 2 to 8 carbon atoms, preferably of 4 to 6 carbon atoms, which include ethylene, propylene, butylene and pentylene, which may be substituted by one or more alkyl groups which include 1-methylpropylene, 1-methylbutylene and the like.

Phenyl as used herein refers to a 6-membered aromatic ring.

The term aryl when used alone means a homocyclic aromatic radical, whether or not fused having 6 to 12 carbon atoms. Preferred aryl groups include phenyl, 1-naphthyl, 2-naphthyl, diphenylmethyl, 9-fluorenyl and the like optionally substituted with one, two or three substituents selected from the group consisting of hydrogen, halogen, trifluoromethyl, cyano, carboxy, amino, alkyl of 1 to 8 carbon atoms, benzylamino, allylamino, alkylamino of 1 to 8 carbon atoms, dialkylamino of 1 to 8 carbon atoms in each alkyl group, alkylthio of 1 to 8 carbon atoms, alkylsulfonyl of 1 to 8 carbon atoms, acetyl, acetamido, phenyl and benzoyl.

The term heterocycle denotes an unsubstituted or substituted 5- or 6-membered heterocyclic ring, independently having from 1 to 3 heteroatoms, which may be fused to another 6-membered heterocyclic or non-heterocyclic ring, especially heteroaromatic rings which may contain 1 to 3, or particularly 1 or 2, hetero-atoms which may be the same or different, optionally substituted with one or more, preferably 1 or 2, substituents which may be the same or different selected from alkyl, especially of 1 or 2 carbon atoms, alkoxy, especially of 1 or 2 carbon atoms, halogen and nitro. Nitrogen, oxygen and sulfur are the preferred heteroatoms. Preferred heterocycles include 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl optionally substituted with one or more, preferably 1 or 2, substituents which may be the same or different selected from alkyl, especially of 1 or 2 carbon atoms, alkoxy, especially of 1 or 2 carbon atoms, halogen and nitro;

It is understood in references to alkylcarbonyloxy (alkyl)C(O)O— of 1 to 8 carbon atoms and alkylcarbonyl (alkyl)C(O)— of 1 to 8 carbon atoms described herein that reference to 1 to 8 carbon atoms describes the length of the alkyl as bonded to the carbonyl carbon. Arylsulfonyl as used herein refers to the radical —$SO_2$aryl where aryl is previously defined.

Arylalkyl as used herein means an aryl-alkyl group in which the aryl and alkyl group are previously defined. Exemplary aralkyl groups include benzyl and phenethyl.

N-Alkylsulfonamido as used herein refers to the radical —$SO_2$NH-(alkyl) where alkyl is 1 to 8 carbon atoms.

N,N,Dialkylsulfonamido as used herein refers to the radical —$SO_2$N(alkyl)$_2$ where each alkyl is independently 1 to 8 carbon atoms.

Carboxamido as used herein refers to —$CONH_2$.

N-Alkyl carboxamido as used herein refers to —CONH(alkyl) of 1 to 8 carbon atoms.

N,N-(dialkyl)carboxamido as used herein refers to —CON(alkyl)$_2$ with each independent alkyl of 1 to 8 carbon atoms.

The organic bases of this invention form non-toxic acid-addition salts with a variety of pharmacologically acceptable organic and inorganic salt-forming reagents. Thus acid-addition salts, formed by admixture of the organic free base with one or more equivalents of an acid, suitably in a neutral solvent, are formed with such acids as sulfuric, phosphoric, hydrochloric, hydrobromic, hydriodic, sulfamic, citric, lactic, malic, succinic, maleic, fumaric, tartaric, acetic, benzoic, gluconic, ascorbic and the like. For the purpose of this invention the free bases are equivalent to their non-toxic acid-addition salts.

Among the preferred compounds of Formula I of this invention are those in the subgroups and pharmaceutically acceptable salts thereof:

i)
  a is not present as an additional bond;
  b is present as an additional bond;
  $R_1$ is not present;
  $R_5$ is present;

ii)
  a is present as an additional bond;
  b is not present as an additional bond;
  $R_1$ is present;
  $R_5$ is not present;

iii)
  a is not present as an additional bond;
  b is present as an additional bond;
  $R_1$ is not present;
  $R_2$ is selected from the group consisting of hydrogen, alkoxy of 1 to 8 carbon atoms, alkylthio of 1 to 8 carbon atoms, alkylsulfonyl of 1 to 8 carbon atoms, arylsulfonyl of 6 to 12 carbon atoms, hydroxy, hydroxyalkyl of 1 to 8 carbon atoms, mercapto, alkylcarbonyloxy of 1 to 8 carbon atoms, amino, cyano, sulfonamido, —N-(alkyl)sulfonamido of 1 to 8 carbon atoms, and halogen;
  Q is selected from
    a) a chain —$(CH_2)_m$—, where said chain is substituted by one or two alkyl, cycloalkyl, arylalkyl, aryl, hydroxy, alkoxy, fluoro, where said chain may contain one or more —CH═CH— linkages, and where said chain may have functions such as —O—, —S—, —$SO_2$—, —NH—, —N-alkyl, N-aryl, and 0 —(C═O)NH— replacing one of the —$CH_2$— groups;
    b) a moiety of the formula

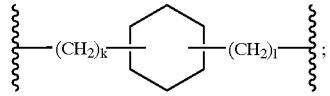

m is an integer 2–10;
  $R_3$ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;
  $R_4$ is selected from hydrogen, halogen and methyl;
  $R_5$ is selected from hydrogen and alkyl of 1 to 8 carbon atoms;

iv)
  a is present as an additional bond;
  b is not present as an additional bond;
  $R_1$ is selected from the group consisting of H, alkyl of 1 to 6 carbon atoms, phenyl, a moiety of the formula:

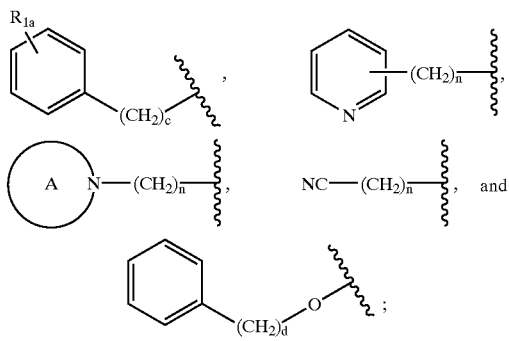

R₂ is selected from the group consisting of hydrogen, alkoxy of 1 to 8 carbon atoms, alkylthio of 1 to 8 carbon atoms, alkylsulfonyl of 1 to 8 carbon atoms, arylsulfonyl, hydroxy, hydroxyalkyl of 1 to 8 carbon atoms, mercapto, alkylcarbonyloxy of 1 to 8 carbon atoms, amino, cyano, sulfonamido, N-(alkyl) sulfonamido of 1 to 8 carbon atoms, and halogen;

Q is selected from
a) a chain —(CH₂)ₘ—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO₂—, —NH—, —N-alkyl, —N-aryl, and —(C=O)NH— replacing one of the —CH₂— groups;
b) a moiety of the formula

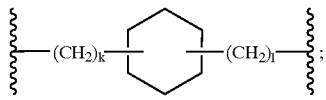

k, l and m are independently selected from an integer of 2 to 10;

R₃ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

R₄ is selected from hydrogen and halogen;
R₅ is not present;

v)
a is not present as an additional bond;
b is present as an additional bond;
R₁ is not present;
R₂ is selected from the group consisting of hydrogen, alkoxy of 1 to 8 carbon atoms, hydroxy, hydroxyalkyl of 1 to 8 carbon atoms, alkylcarbonyloxy of 1 to 8 carbon atoms, amino, cyano, and halogen;
Q is selected from the group consisting of a chain —(CH₂)ₘ—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO₂—, —NH—, —N-alkyl, —N-aryl, and —(C=O)NH— replacing one of the —CH₂— groups;
k, l and m are independently selected from an integer 2 to 5;
R₃ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-pyrazol-1-yl, 2-thiazolyl, 2-furanyl, 2-thiophenyl, pyrimidinyl, quinolinyl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;
R₄ is selected from hydrogen and halogen;
R₅ is selected from hydrogen and alkyl of 1 to 8 carbon atoms;

vi)
a is present as an additional bond;
b is not present as an additional bond;
R₅ is not present;
R₁ is selected from the group consisting of alkyl of 1 to 6 carbon atoms, phenyl, a moiety of the formula:

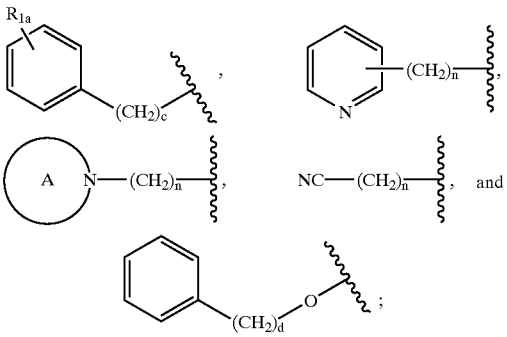

n is an integer of 2 to 6;
R₂ is selected from the group consisting of hydrogen, alkoxy of 1 to 8 carbon atoms, hydroxy, hydroxyalkyl of 1 to 8 carbon atoms, alkylcarbonyloxy of 1 to 8 carbon atoms, amino, cyano, and halogen;
Q is selected from the group consisting of a chain —(CH₂)ₘ—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO₂—, —NH—, —N-alkyl, —N-aryl, and —(C=O)NH— replacing one of the —CH₂— groups;
k, l and m are independently selected from an integer 2 to 5;
R₃ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-pyrazol-1-yl, 2-thiazolyl, 2-furanyl, 2-thiophenyl, pyrimidinyl, quinolinyl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

R₄ is selected from hydrogen and halogen.

Among the specifically preferred compounds of Formula I of this invention for the method of treating, inhibiting or controlling ras-associated diseases by inhibiting farnesyl-protein transferase enzyme including pharmaceutically acceptable salts thereof are those set forth below:

N-[3-(1H-imidazol-1-yl)-propyl]-N-octyl-benz[cd]indol-2-amine, fumarate (1:2),

N-[4-(1H-imidazol-1-yl)-butyl]-6-iodo-benz[cd]indol-2-amine, 1,2-dihydro-2-[[3-(1H-imidazol-1-yl)propyl]imino]-1-methyl-benz[cd]indole-6-methanol, fumarate (1:1), N-[1-(phenylmethyl)benz[cd]indol-2(1H)-ylidene]-1H-imidazole-1-butanamine, fumarate (1:2), 2-[[3-(1H-imidazol-1-yl)propyl]imino]-benz[cd]indole-1(2H)-pentanenitrile, N,N'-[1,3-propanediylbis(benz[cd]indol-1(2H)-yl-2-ylidene)]bis-1H-imidazole-1-propanamine, N-(1-hexylbenz[cd]indol-2(1H)-ylidene)-1H-imidazole-1-propanamine, fumarate (1:2), N-(1-hexylbenz[cd]indol-2(1H)-ylidene)-3-pyridinebutanamine, fumarate (2:3), N-[1-(3-pyridinylmethyl)benz[cd]indol-2(1H)-ylidene)-1H-imidazole-1-propanamine, N-[1-(phenylmethyl)benz[cd]indol-2(1H)-ylidene]-1H-imidazole-1-propanamine, fumarate (1:2), N-[1-(3-phenylpropyl)benz[cd]indol-2(1H)-ylidene]-1H-imidazole-1-propanamine, fumarate (1:2), N-[1-(3-phenoxypropyl)benz[cd]indol-2-(1H)-ylidene]-1H-imidazole-1-propanamine, dihydrochloride, N-[1-[(3-methoxyphenyl)methyl]benz[cd]indol-2(1H)-ylidene]-1H-imidazole-1-propanamine, N-[1-[[3-(trifluoromethyl)phenyl]methyl]benz[cd]indol-2(1H)-ylidene]-1H-imidazole-1-propanamine, N-[1-[(4-chlorophenyl)methyl]benz[cd]indol-2(1H)-ylidene]-1H-imidazole-1-propanamine, N-(1-phenylbenz[cd]indol-2(1H)-ylidene)-1H-imidazole-1-propanamine, 2-[4-(1H-imidazol-1-ylmethyl)-1-piperidinyl]-benz[cd]indole, monohydriodide, N-[6-chloro-1-(phenyl-methyl)benz[cd]indol-2(1H)-ylidene]-1H-imidazole-1-propanamine, N-[6-chloro-1-(phenylmethyl)benz[cd]indol-2(1H)-ylidene]-3-pyridinethanamine, N-(1-(4-chlorobenzyl)-6-iodobenzo[cd]indol-2-(1H)-ylidene)-3-(1H-imidazol-1-yl)-1-propanamine, 3-(1H-imidazol-1-yl)-N-(6-iodobenzo[cd]indol-2(1H)-ylidene)-1-propanamine, N-benzyl-N-(6-iodobenzo[cd]lindol-2(1H)-ylidene)amine, and (2E,6E)-N-(benzo[cd]indol-2(1H)-ylidene)-3,7,11-trimethyl-2,6,10-dodecatrien-1-amine.

Additionally, this invention provides a method of treatment, by administration of an effective amount of compounds of Formula I, of ras oncogene-dependent tumors, which include cancers of the pancreas, colon, bladder, and thyroid; a method of controlling metastasis, suppressing angiogenesis, and inducing apoptosis; a method of treating Ras-associated proliferative diseases other than cancer, which include restenosis, neuro-fibromatosis, endometriosis, and psoriasis The compounds of Formula I may also inhibit prenylation of proteins other than Ras, and thus provide a method of treatment of diseases associated with other prenyl modifications of proteins. The compounds of Formula I inhibit farnesyl-protein transferase and the farnesylation of the oncogene protein Ras. Thus, this invention further provides a method of inhibiting farnesyl protein transferase, (e.g., Ras farnesyl protein transferase) in mammals, especially humans, by the administration of an effective amount of the compounds of Formula I. The administration of the compounds of this invention to patients, to inhibit farnesyl protein transferase, is useful in the treatment of the cancers and other diseases described below. This invention provides a method for inhibiting or treating the abnormal growth of cells, including transformed cells by administering an effective amount of a compound of Formula I. Abnormal growth of cells refers to cell growth independent of normal regulatory mechanisms (e.g., loss of contact inhibition). This includes abnormal growth of tumor cells (tumors) expressing an activated Ras oncogene; tumor cells in which the Ras protein is activated as a result of oncogenic mutation in another gene; and benign and malignant cells of other proliferative diseases in which aberrant Ras activation occurs.

This invention also provides a method for inhibiting or treating tumor growth by administering an effective amount of a compound of Formula I, described herein, to a mammal (e.g., a human) in need of such treatment. In particular, this invention provides a method for inhibiting or treating the growth of tumors expressing an activated Ras oncogene by administration of an effective amount of a compound of Formula I. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form-with said inhibition or treatment being accomplished by the administration of an effective amount of a compound of Formula I, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the compounds of Formula I.

Additionally, this invention provides a method of inhibition or treating the abnormal growth of cells, by administration of an effective amount of compounds of Formula I, of ras-oncogene-dependent tumors, which tumors include cancers of the pancreas, colon, bladder, and thyroid. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that the compounds of Formula I inhibit Ras farnesyl-protein transferase, and thus antiproliferative activity of ras-transformed cells and other prenyl modifications of proteins.

DETAILED DESCRIPTION OF THE INVENTION

Compounds of this invention are prepared according to the procedures defined herein as Method A and described in U.S. Pat. Nos. 5,081,131, 5,079,247, 4,728,663, and 4,261,896, which are hereby incorporated herein by reference. In addition, compounds of this invention can be prepared according to Methods B and C as described in Scheme I, where $R_1$, $R_2$, $R_3$, $R_4$, $R_5$ and Q are hereinbefore defined.

Scheme I

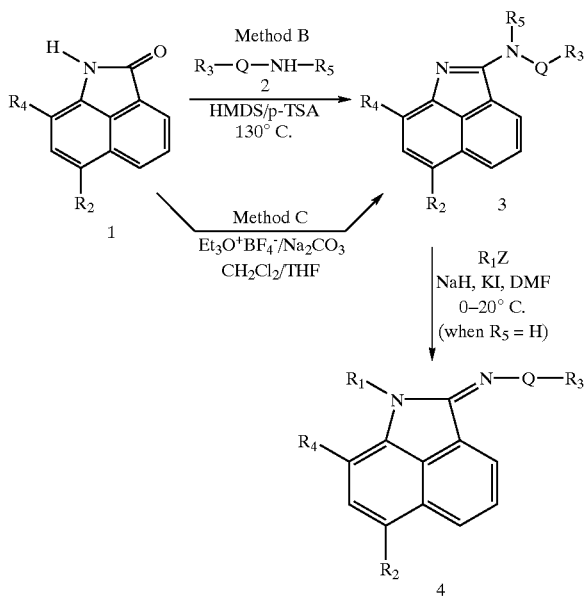

Referring to Method B, a substituted benz[cd]indol-2 (1H)-one 1 and amine 2 where $R_3$, $R_5$ and Q are hereinbefore defined were stirred in hexamethyldisilazane for 1 to 4 hours at 120–130° C. in the presence of p-toluenesulfonic acid monohydrate to give amine 3. Alternatively, using Method C, a solution of substituted benz[cd]indol-2(H)one 1 in tetrahydrofuran was stirred at room temperature for 1 to 4 hours in the presence of a methylene chloride solution of triethyloxonium tetrafluoroborate followed by the addition of solid $Na_2CO_3$ and amine 2 and continued stirring at room temperature for 18 to 24 hours to afford amine 3.

Reaction of amine 3 where $R_5$ is H, with sodium hydride in a polar solvent which includes but is not limited to N,N-dimethylformamide in the presence of potassium iodide followed by the addition of $R_1Z$ where Z is a leaving group which includes halogen, triflate, mesylate, tosylate, methyl sulfamyl, tolene sulfamyl and the like at 0 to 20° C. for to up 18 hours affords amine 4.

Pharmacological Test Procedures:

The ability of the compounds of this invention to inhibit FPTase was evaluated in the standard pharmacological in vitro test procedures described below. Data for representative examples is summarized in Table I and Table II.

Enzyme test procedure: The FPTase inhibition in vitro assay was performed according to the method as described by James, G. L., Brown, M. S., and Goldstein, J. L., *Methods in Enzymology*, 1995, 255, 38–46; and Garcia, M. A., et al., *J. Biol. Chem.*, 1993, 268, 18415–18420.

Materials—Purified FPTase (Moomaw, J. F. and Casey, P. J., *J. Biol. Chem.*, 1992, 267, 17438–17443), purified $His_6$-Ras, inhibitor compounds at 10 mg/ml or 10 mM in 100% DMSO, $^3$H-FPP (50,000 dpm/pmol) Amersham, TCA/SDS (6%/2%), TCA (6%), Glass fiber filters (0.22–0.45 m), vacuum manifold or 96 well filtration plates.

Methods—1. Dilute FPTase inhibitors from stock solutions to 2.5× in 2.5% DMSO, 10 mM DTT, 0.5% octyl-B-glucoside. 2. Solution #1 is added to FPTase reaction in a volume of 20 ml. 3. Standard reaction mix, 50 ml, contains 50 mM Tris (7.5),10 mM $ZnCl_2$, 3 mM $MgCl_2$, 20 mM KCl, 5 mM DTT, 0.2% octyl-B-glucoside, 1% DMSO, 40 mM $His_6$-Ras, 10 ng FPTase, and various concentrations of FPTase inhibitors. 4. Incubate for 30–90 min at 25° C. 5. Stop reactions with TCA/SDS (6%/2%), hold at 4° C. for 45–60 min. 6. Filter by manifold or 96 well plate, wash filter 3–5× with TCA (6%). 7. Add scintillant to filters, measure $^3$H-FPP incorporation into Ras protein.

Analysis of Results—Percent inhibition by test compounds is determined by the following:

(cpm from precipitated Ras with test compounds)−(background cpm)×100=% inhibition.

(cpm from precipitated Ras without test compounds)−(background cpm)

Cell-based test procedure: The Tumor inhibition in vitro assay was performed according to method as described by P. Skehan, R. Storeng, D. Scudiero, A. Monks, J. McMohan, D. Vistica, J. Warren, H. Bokesh, S. Kenney, and M. R. Boyd, *J. Natl. Cancer Instit.*, 1990, 82 (13), 1107–1112; L. V. Rubinstein, R. H. Shoemaker, K. D. Paull, R. M. Simon, S. Tosini, P. Skehan, D. A. Scudiero, A. Monks, and M. R. Boyd, *J. Natl. Cancer Instit.*, 1990, 82 (13), 1113–1118; A. Monks, et al., *J. Natl. Cancer Instit.*, 1991, 83, 757–766; M. R. Boyd and K. D. Paull, *Drug Development Res.*, 1995, 34, 91–109; and S. P. Fricker and R. G. Buckley, *Anticancer Research*, 1996, 16, 3755–3760.

Materials—Cell Lines: Human tumor cell lines DLD-1 and LoVo; ras-transformed rat fibroblast cell lines, RAT-H-ras and RAT-K-ras (growth inhibited by standard FPTase inhibitors), and the parent cell line RAT-2 (resistant to standard FPTase inhibitors). Cell Media: RPMI 1640 (or DMEM medium and McCoy's medium) with 10% Fetal Bovine Serum supplemented with L-glutamine and Pennicilin/Streptomycin. Compounds: Supplied usually as a 10 mM stock in 100% DMSO. Normal Saline: 150 mM NaCl Trichloroacetic Acid (TCA): 50% (w/v) in water. Sulforhodamine (SRB): 0.4% (w/v) in 1% Acetic Acid. Tris Base: 10 mM in water.

Methods—Cells are plated at 2000 cells per well, per 200 μl media, and allowed to adhere overnight at 37° C. At 24 h post plating, compounds are added directly at a volume of 0.5 μl. Compound is first diluted in DMSO to generate concentrations of compound or reference standard of: 1, 5, 10 and 25 μM. Dilutions can be made in an identical 96 well plate so that compounds can be added using a multichannel micropipettor set at 0.5 μl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 μl of normal saline is then added to each well using an 8 well multichannel pipettor, followed by the careful addition of 50 μl of 50% TCA. The plates are then incubated for 2 h at 4° C., after which the supernatant is removed using the same technique as above and the plates washed twice with 200 μl water. The plates are then air dried and 50 μl of SRB stock solution is carefully added so that the entire bottom of each well is covered. This again can be used using an 8 well multichannel pipettor. The SRB is incubated with fixed cells for 15 min at room temperature, after which the SRB is removed with the manifold as described above and the plates washed twice with 350 μl of 1% acetic acid per well each time. The plates are then air dried after which the bound SRB is released from protein by the addition of 200 μl of Tris base. Resolubilizing the SRB is aided by placing the plates on a rotator for 15–30 min. The absorbence of each well is determined at 550 or 562 nm using a microtiter plate reader.

Analysis of Results—Each compound or dilution thereof is performed in triplicate. Outliers are identified by visual inspection of the data. Each plate should have a control (vehicle only). A standard curve is constructed by plotting the concentration of compound against the average absorbance calculated at that concentration. A curve is plotted and the concentration at which the curve passes through the 50% absorbance mark seen in the control well is the $IC_{50}$ calculated for that compound.

TABLE I in vitro FPTase Inhibition

| Ex. # | $IC_{50}$ (vs. H-Ras)* μM | $IC_{50}$ (vs. K-Ras)* μM |
|---|---|---|
| 1 | 1.20 | 8.0 |
| 2 | 6.70 | — |
| 3 | 2.50 | >10 |
| 4 | 2.80 | >10 |
| 5 | 0.32 | 4.8 |
| 6 | 2.25 | >10 |
| 7 | 1.80 | >10 |
| 8 | 2.40 | >10 |
| 9 | 2.00 | >10 |
| 10 | 0.65 | 10.0 |
| 11 | 0.60 | 9.5 |
| 12 | 1.50 | 10.0 |
| 13 | 0.40 | >10 |
| 14 | 0.20 | 8.5 |
| 15 | 0.18 | 10.0 |
| 16 | 2.50 | >10 |
| 17 | 2.00 | >10 |
| 18 | 0.80 | >10 |
| 19 | 0.10 | >10 |
| 20 | 0.90 | 10.0 |

*H-Ras or K-Ras used as substrates for farnesylation

TABLE II in vitro Cell Growth Inhibition

| Ex. # | Rat-H $IC_{50}$ μM | Rat-K $IC_{50}$ μM | Rat-2 $IC_{50}$ μM | DLD-1 $IC_{50}$ μM | LoVo $IC_{50}$ μM |
|---|---|---|---|---|---|
| 3 | 19 | 26 | >40 | >40 | 26 |
| 4 | 12 | 16 | 23 | 22 | 14 |
| 6 | 4 | 2 | 13 | 6 | 6 |
| 7 | 6 | 4 | 18 | 20 | 14 |
| 8 | 6 | 7 | 20 | 15 | 6 |
| 11 | 7 | 4 | 17 | 18 | 6 |
| 13 | 4 | 3 | 17 | 17 | 6 |
| 14 | 4 | 2 | 5 | 5 | 5 |
| 15 | 4 | 4 | 19 | 19 | 7 |
| 16 | >40 | 38 | >40 | >40 | >40 |
| 19 | >40 | >40 | >40 | >40 | >40 |
| 20 | 1 | 1 | 2 | 2 | 2 |

Based on the results of these standard pharmacological test procedures, the compounds of this invention are useful as agents for treating, inhibiting or controlling ras-associated diseases by inhibiting farnesyl-protein transferase enzyme, when administered in amounts ranging from about 10 to about 200 mg/kg of body weight per day. A preferred regimen for optimum results would be from about mg to about 100 mg/kg of body weight per day and such dosage units are employed that a total of from about 100 mg to about 1000 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes. The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures therof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The following examples are representative compounds of this invention which are useful in inhibiting FPTase. The compounds of this invention were prepared by the procedures of Method A, known in the art, and described in U.S. Pat. Nos. 5,081,131, 5,079,247, 4,728,663, and 4,261,896, or according to the procedures of Examples 20–22 (Methods B and C).

EXAMPLE 1

N-[3-(1H-Imidazol-1-yl)-propyl]-N-octyl-benz[cd]indol-2-amine, Fumarate (1:2)

EXAMPLE 2

N-[4-(1H-Imidazol-1-yl)-butyl]-6-iodo-benz[cd]indol-2-amine

The product of the example was prepared using the procedure of Method A and additionally prepared using the procedure of Method B as described in Example 21 and the procedure of Method C as described in Example 23.

EXAMPLE 3

1,2-Dihydro-2-[[3-(1H-imidazol-1-yl)propyl]imino]-1-methyl-benz[cd]indole-6-methanol, Fumarate (1:1)

EXAMPLE 4

N-[1-(Phenylmethyl)benz[cd]indol-2(1H)-ylidene]-1H-imidazole-1-butanamine, Fumarate (1:2)

EXAMPLE 5

2-[[3-(1H-Imidazol-1-yl)propyl]imino]-benz[cd]indole-1(2H)-pentanenitrile

EXAMPLE 6

N,N'-[1,3-Propanediylbis(benz[cd]indol-1(2H)-yl-2-ylidene)]bis-1H-imidazole-1-propanamine

EXAMPLE 7

N-(1-Hexylbenz[cd]indol-2(1H)-ylidene)-1H-imidazole-1-propanamine, Fumarate (1:2)

EXAMPLE 8

N-(1-Hexylbenz[cd]indol-2(1H)-ylidene)-3-pyridinebutanamine, Fumarate (2:3)

EXAMPLE 9

N-[1-(3-Pyridinylmethyl)benz[cd]indol-2(1H)-ylidene]-1H-imidazole-1-propanamine

EXAMPLE 10

N-[1-(Phenylmethyl)benz[cd]indol-2(1H)-ylidene]-1H-imidazole-1-propanamine, Fumarate (1:2)

EXAMPLE 11

N-[1-(3-Phenylpropyl)benz[cd]indol-2(1H)-ylidene]-1H-imidazole-1-propanamine, Fumarate (1:2)

EXAMPLE 12

N-[1-(3-Phenoxypropyl)benz[cd]indol-2-(1H)-ylidene]-1H-imidazole-1-propanamine, Dihydrochloride

EXAMPLE 13

N-[1-[(3-Methoxyphenyl)methyl]benz[cd]indol-2(1H)-ylidene]-1H-imidazole-1-propanamine

EXAMPLE 14

N-[1-[[3-(Trifluoromethyl)phenyl]methyl]benz[cd]indol-2(1H)-ylidene]-1H-imidazole-1-propanamine

EXAMPLE 15

N-[1-[(4-Chlorophenyl)methyl]benz[cd]indol-2(1H)-ylidene]-1H-imidazole-1-propanamine

EXAMPLE 16

N-(1-Phenylbenz[cd]indol-2(1H)-ylidene)-1H-imidazole-1-propanamine

EXAMPLE 17

2-[4-(1H-Imidazol-1-ylmethyl)-1-piperidinyl]-benz[cd]indole, Monohydriodide

The product of the example was prepared using the procedure of Method A and additionally prepared using the procedure of Method B as described in Example 21 and the procedure of Method C as described in Example 23.

EXAMPLE 18

N-[6-Chloro-1-(phenyl-methyl)benz[cd]indol-2(1H)-ylidene]-1H-imidazole-1-propanamine

EXAMPLE 19

N-[6-Chloro-1-(phenylmethyl)benz[cd]indol-2(1H)-ylidene]-3-pyridinethanamine

EXAMPLE 20

N-(1-(4-Chlorobenzyl)-6-iodobenzo[cd]indol-2-(1H)-ylidene)-3-(1H-imidazol-1-yl)-1-propanamine Method 1. Following the procedure of Examples 3–16, 18, 19, from patents listed above.

Method 2. Synthesis from product of Example 21: To a stirred suspension of NaH (60% in mineral oil, washed with hexane and dried in vacuum; 60 mg, 1.5 mmol) in DMF (3.5 ml), the compound from Example 21 (N-[3-(1H-imidazol-1-yl)-propyl]-6-iodo-benz[cd]indol-2-amine; 300 mg, 0.75 mmol) was added at 0°. The resulting mixture was stirred for 30 min at 0° and KI (20 mg, 0.12 mmol) and 4-chlorobenzyl chloride (145 mg, 0.9 mmol) were added at the same temperature. The reaction mixture was warmed up to 20° during 30 min and stirred for an additional 40 min at the same temperature. Water (10 ml) was added and the mixture was extracted with EtOAc (40 ml). The organic solution was washed with water (2×15 ml) and brine (2×15 ml) and dried over $MgSO_4$. Filtration and evaporation provided the crude amidine. Crystallization from EtOAc-hexane gave 270 mg (68%) of a yellow solid which was characterized as [1-(4-Chloro-benzyl)-6-iodo-1H-benzo[cd]indol-2-ylidene]-(3-imidazol-1-yl-propyl)-amine: mp 146–1480; NMR ($CDCl_3$) δ 2.23 (m, 2H), 3.76 (t, J=6.8, 2H), 4.16 (t, J=7.4, 2H), 5.11 (s, 2H), 6.40 (d, J=8.47, 1H), 6.85 (s, 1H), 7.03 (s, 1H), 7.26 (m, 4H), 7.39 (s, 1H), 7.70 (m, 1H), 8.83 (m, 2H), 8.88 (d, J=9.2, 1H). MS m/z 527 and 529 ((M+H calcd. for $C_{24}H_{20}ClIN_4$ 526 and 528.

EXAMPLE 21

3-(1H-Imidazol-1-yl)-N-(6-iodobenzo[cd]indol-2(1H)-ylidene)-1-propanamine

Method A. Following Example 17 or Method A. in Example 2, from patents listed above.

Method B. 6-Iodo-1H-benzo[cd]indol-2-one (1.1 g, 3.73 mmol), 1-(3-aminopropyl)-imidazole (1.2 g, 9.6 mmol) and p-toluenesulfonic acid monohydrate (0.1 g, 0,52 mmol) were stirred in hexamethyldisilazane (5 ml) for 2 h at 130°.

The reaction mixture was cooled down to 25° and water (40 ml) was added. The resulting mixture was extracted with EtOAc (2×40 ml). The combined organic solution was washed with water (20 ml), and brine (2×20 ml), and dried over $MgSO_4$. Filtration and evaporation provided the crude amidine. Crystallization from EtOAc-ether gave 1.57 g (80%) of an orange colored solid which was characterized as N-[3-(1H-imidazol-1-yl)-propyl]-6-iodo-benz[cd]indol-2-amine: mp 185–188°; NMR ($CDCl_3$) δ 2.30 (m, 2H), 3.64 (t, J=7.2, 2H), 4.18 (t, J=7.9, 2H), 6.90 (d, J=8.1, 1H), 7.04 (m, 2H), 7.60 (s, 1H), 7.67 (m, 1H), 7.84 (m, 2H), 8.05 (d, J=7.6, 1H); MS m/z 403 (M+H calcd. for $C_{17}H_{16}IN_4$ 403).

The product of the example was additionally prepared using the procedures of Method C as described in Example 23.

EXAMPLE 22

N-Benzyl-N-(6-iodobenzo[cd]indol-2(1H)-ylidene)amine

The product of the example was prepared using the procedures of Method A.

The product of the example was also prepared using the procedures of Method B as described in Example 21. 6-Iodo-1H-benzo[cd]indol-2-one (0.2 g, 0.68 mmol), benzylamine hydrochloride (0.195 g, 1.36 mmol) and p-toluenesulfonic acid monohydrate (0.01 g, 0.052 mmol) were stirred in hexamethyldisilazane (0.45 ml) for 3 h at 130°. Workup as before provided the crude product. Crystallization from EtOAc-ether gave 0.172 g (66%) of a dark yellow solid: mp 160–163°; NMR (CDCl$_3$) δ 4.90 (s, 2H), 6.99 (d, J=7.3, 1H), 7.36 (m, 3H), 7.46 (m, 2H), 7.62 (m, 1H), 7.78 (m, 1H), 7.87 (m, 2H). MS (EI) m/z 385 (M+H calcd. for $C_{18}H_{14}IN_2$ 385).

The product of the example was additionally prepared using the procedures of Method C as described in Example 23.

EXAMPLE 23

(2E,6E)-N-(Benzo[cd]indol-2(1H)-ylidene)-3,7,11-trimethyl-2,6,10-dodecatrien-1-amine The product of the example was prepared using the procedures of Method A.

The product of the example was also prepared using the procedures of Method B as described in Example 21.

Method C. To a stirred solution of 1H-benzo[cd]indol-2-one (0.15 g, 0.89 mmol) in THF (1ml), a 1.0 M solution of triethyloxonium tetraflouroborate in CH$_2$Cl$_2$ (1ml, 1.0 mmol) was added at 25° and the resulting mixture was stirred for 3 h at the same temperature. Solid Na$_2$CO$_3$ (0.212 g, 2.0 meq) and a solution of α,α-farnesyl amine (0.22 g, 1.0 mmol) in THF (1 ml) were added at 25° and the reaction mixture was stirred for 18 h at the same temperature. Ethyl acetate (30 ml) was added and the mixture was washed with water (2×10 ml and dried over MgSO$_4$. Filtration and evaporation provided the crude product. Chromatography on silica gel, eluting with EtOAc-hexane (1:1), gave 0.27 g (61%) of a yellow oil which was identified as (1H-benzo[cd]indol-2-ylidene)-[(E,E)-3,7,11-trimethyl-2,6,10-dodecatrien-1-yl]-amine: NMR (CDCl$_3$) δ 1.59 (s, 3H), 1.60 (s, 3H), 1.68 (d, J=0.4, 3H), 1.76 (s, 3H), 1.93–2.20 (m, 8H), 4.34 (d, J=6.7, 2H), 4.96–5.04 (m, 2H), 5.48 (m, 1H), 6.96–8.12 (m, 7H). MS (EI) m/z 373 (M+H calcd. for $C_{26}H_{33}N_2$ 373).

What is claimed is:

1. A method of treating, inhibiting or controlling a ras-associated disease by inhibiting farnesyl-protein transferase (FPTase) enzyme in a mammal in need thereof, which comprises administering to said mammal an effective amount of a compound of Formula I:

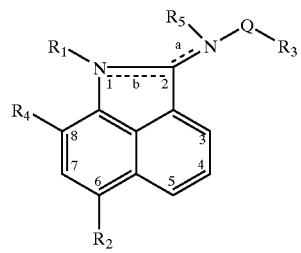

Formula I wherein:
the dotted line ------ at position a is an optional additional bond;
the dotted line ------ at position b is an optional additional bond;
R$_1$ is selected from the group consisting of H, alkyl of 1 to 6 carbon atoms, phenyl, and a moiety of the following:

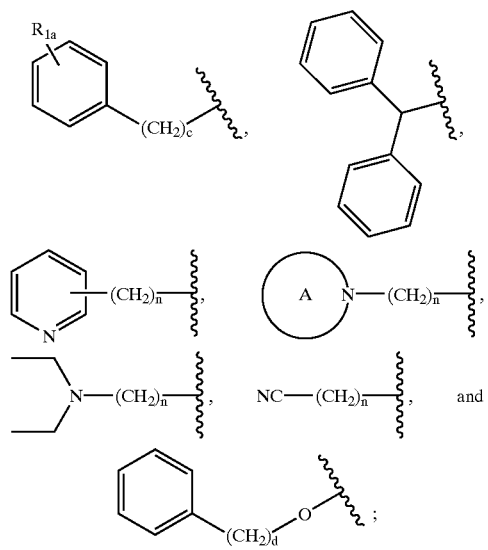

R$_{1a}$ is selected from alkoxy of 1 to 8 carbon atoms, trifluoromethyl and halogen;
c is an integer of 0 to 3;
d is an integer of 1 to 3;
n is an integer of 1 to 6;
A is a monocyclic ring having 5 or 6 ring atoms optionally having saturated or unsaturated bonds and containing 1 or 2 nitrogen atoms and 0 or 1 oxygen atoms;
R$_2$ is selected from the group consisting of hydrogen, alkoxy of 1 to 8 carbon atoms, alkylthio of 1 to 8 carbon atoms, alkylsulfonyl of 1 to 8 carbon atoms, arylsulfonyl of 6 to 12 carbon atoms, hydroxy, hydroxyalkyl of 1 to 8 carbon atoms, mercapto, alkylcarbonyloxy of 1 to 8 carbon atoms, amino, mono(alkyl)amino of 1 to 8 carbon atoms, di(alkyl)amino of 1 to 16 carbon atoms, (alpha, omega-alkylene)amino of 2 to 8 carbon atoms, alkyl of 1 to 8 carbon atoms, arylalkyl of 7 to 20 carbon atoms, cycloalkyl of 3 to 10 carbon atoms, cycloalkylalkoxy of 3 to 10 carbon atoms, alkylcarbonyl of 1 to 8 carbon atoms, arylcarbonyl of 6 to 12 carbon atoms, cyano, sulfonamido, N-alkylsulfonamido of 1 to 8 carbon atoms, N,N-

(dialkyl)sulfonamido of 2 to 16 carbon atoms, alpha-hydroxyalkyl of 1 to 8 carbon atoms, alpha-aminoalkyl of 1 to 8 carbon atoms, alpha-alkylaminoalkyl of 2 to 16 carbon atoms, alpha-(dialkyl)amino(alkyl) of 3 to 24 carbon atoms, carboxamido, N-(alkyl)carboxamido of 1 to 8 carbon atoms, N,N-(dialkyl)carboxamido of 2 to 16 carbon atoms, and halogen;

Q is selected from
a) a chain —$(CH_2)_m$— optionally containing one or more —CH=CH— or —C≡C— linkages and further optionally replacing one of the chain —$CH_2$— groups with —O—, —S—, —$SO_2$—, —NH—, —N-alkyl of 1 to 8 carbon atoms, —N-aryl of 6 to 12 carbon atoms, or —(C=O)NH— and further optionally substituting said chain with substitutents selected from alkyl of 1 to 8 carbon atoms, cycloalkyl of 3 to 10 carbon atoms, arylalkyl of 7 to 20 carbon atoms, aryl of 6 to 12 carbon atoms, hydroxy, alkoxy of 1 to 8 carbon atoms, and fluoro; or
b) a moiety of the formula

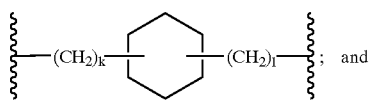 and c) a moiety of the formula

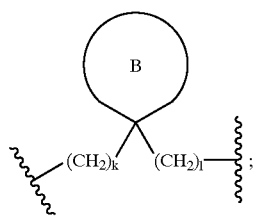

k, l and m are independently selected from an integer of 1 to 12;

B is a monocyclic ring having 3 to 10 ring atoms;

$R_3$ is selected from hydrogen, and a substituted or unsubstituted heterocycle;

$R_4$ is selected from hydrogen, halogen, and alkyl of 1 to 6 carbon atoms;

$R_5$ is selected from hydrogen and alkyl of 1 to 8 carbon atoms;

$R_5$ and Q taken together with the nitrogen atom to which they are attached form a monocyclic ring having the moiety

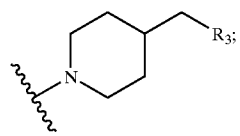

provided that at either position a or b is present an additional bond and if at b, is present an additional bond, $R_1$ is not present and a is not present, and if at a, is present an additional bond, $R_5$ is not present and b is not present;

or a pharmaceutically acceptable salt thereof.

2. The method of claim 1 wherein
a is not present as an additional bond;
b is present as an additional bond;
$R_1$ is not present;
$R_5$ is present;
or a pharmaceutically acceptable salt thereof.

3. The method of claim 1 wherein
a is present as an additional bond;
b is not present as an additional bond;
$R_1$ is present;
$R_5$ is not present;
or a pharmaceutically acceptable salt thereof.

4. The method of claim 1 wherein
a is not present as an additional bond;
b is present as an additional bond;
$R_1$ is not present;
$R_2$ is selected from the group consisting of hydrogen, alkoxy of 1 to 8 carbon atoms, alkylthio of 1 to 8 carbon atoms, alkylsulfonyl of 1 to 8 carbon atoms, arylsulfonyl of 6 to 12 carbon atoms, hydroxy, hydroxyalkyl of 1 to 8 carbon atoms, mercapto, alkylcarbonyloxy of 1 to 8 carbon atoms, amino, cyano, sulfonamido, N-(alkyl)sulfonamido of 1 to 8 carbon atoms, and halogen;

Q is selected from
a) a chain —$(CH_2)_m$—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —$SO_2$—, —NH—, —N-alkyl, —N-aryl, and —(C=O)NH— replacing one of the —$CH_2$— groups;
b) a moiety of the formula

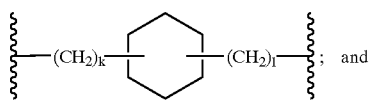

m is an integer 2–10;

$R_3$ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

$R_4$ is selected from hydrogen, halogen and methyl;

$R_5$ is selected from hydrogen and alkyl of 1 to 8 carbon atoms;

or a pharmaceutically acceptable salt thereof.

5. The method of claim 1 wherein
a is present as an additional bond;
b is not present as an additional bond;
$R_1$ is selected from the group consisting of H, alkyl of 1 to 6 carbon atoms, phenyl, a moiety of the formula:

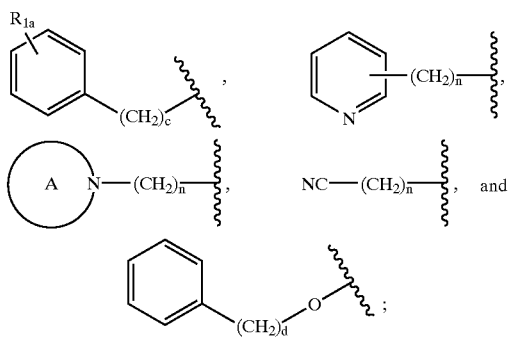

R₂ is selected from the group consisting of hydrogen, alkoxy of 1 to 8 carbon atoms, alkylthio of 1 to 8 carbon atoms, alkylsulfonyl of 1 to 8 carbon atoms, arylsulfonyl, hydroxy, hydroxyalkyl of 1 to 8 carbon atoms, mercapto, alkylcarbonyloxy of 1 to 8 carbon atoms, amino, cyano, sulfonamido, N-(alkyl)sulfonamido of 1 to 8 carbon atoms, and halogen;

Q is selected from
a) a chain —(CH$_2$)$_m$—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO$_2$—, —NH—, —N-alkyl, N-aryl, and —(C=O)NH— replacing one of the —CH$_2$— groups;
b) a moiety of the formula

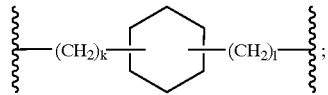

k, l and m are independently selected from an integer of 2 to 10;

R$_3$ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-benzotriazol-1-yl, 1H-pyrazol-1-yl, 1H-1,2,3-triazol-1-yl, 1H-1,2,4-triazol-1-yl, 2H-1,2,3-triazol-4-yl, 2-thiazolyl, 2-furanyl, 2-thiophenyl, pyrimidinyl, quinolinyl, 1,3,4-thiadiazol-2-yl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

R$_4$ is selected from hydrogen and halogen;
R$_5$ is not present;

or the pharmaceutically acceptable salts thereof.

6. The method of claim 1 wherein
a is not present as an additional bond;
b is present as an additional bond;
R$_1$ is not present;
R$_2$ is selected from the group consisting of hydrogen, alkoxy of 1 to 8 carbon atoms, hydroxy, hydroxyalkyl of 1 to 8 carbon atoms, alkylcarbonyloxy of 1 to 8 carbon atoms, amino, cyano, and halogen;
Q is selected from the group consisting of a chain —(CH$_2$)$_m$—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO$_2$—, —NH—, —N-alkyl, —N-aryl, and —(C=O)NH— replacing one of the —CH$_2$— groups;

k, l and m are independently selected from an integer 2 to 5;

R$_3$ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-pyrazol-1-yl, 2-thiazolyl, 2-furanyl, 2-thiophenyl, pyrimidinyl, quinolinyl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

R$_4$ is selected from hydrogen and halogen;
R$_5$ is selected from hydrogen and alkyl of 1 to 8 carbon atoms;

or the pharmaceutically acceptable salts thereof.

7. The method of claim 1 wherein
a is present as an additional bond;
b is not present as an additional bond;
R$_5$ is not present;
R$_1$ is selected from the group consisting of alkyl of 1 to 6 carbon atoms, phenyl, a moiety of the formula:

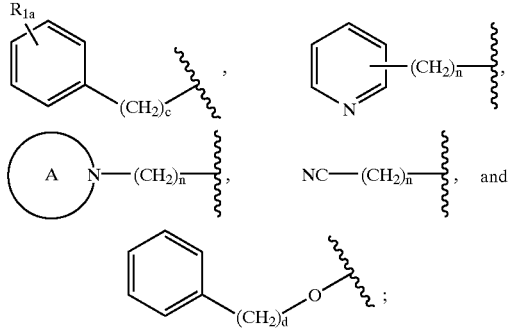

n is an integer of 2 to 6;

R$_2$ is selected from the group consisting of hydrogen, alkoxy of 1 to 8 carbon atoms, hydroxy, hydroxyalkyl of 1 to 8 carbon atoms, alkylcarbonyloxy of 1 to 8 carbon atoms, amino, cyano, and halogen;

Q is selected from the group consisting of a chain —(CH$_2$)$_m$—, where said chain is substituted by one or two alkyl, cycloalkyl, arylalkyl, aryl, hydroxy, alkoxy, fluoro, where said chain may contain one or more —CH=CH— linkages, and where said chain may have functions such as —O—, —S—, —SO$_2$—, —NH—, —N-alkyl, —N-aryl, and —(C=O)NH— replacing one of the —CH$_2$— groups;

k, l and m are independently selected from an integer 2 to 5;

R$_3$ is selected from hydrogen, unsubstituted or substituted 1H-imidazol-1-yl, 1H-imidazol-4-yl, 2-, 3-, and 4-pyridyl, benzimidazol-1-yl, 1H-indol-1-yl, 1H-indazol-1-yl, 1H-pyrazol-1-yl, 2-thiazolyl, 2-furanyl, 2-thiophenyl, pyrimidinyl, quinolinyl, 2-pyrazinyl, 3- and 4-pyridazinyl, 1- and 2-pyrrol-1-yl, optionally substituted with 1 or 2, substituents which may be the same or different selected from alkyl, especially of 1 or 2 carbon atoms, alkoxy, especially of 1 or 2 carbon atoms, halogen and nitro;

$R_4$ is selected from hydrogen and halogen;

or the pharmaceutically acceptable salts thereof.

8. The method of claim 1 wherein the compound is selected from the group consisting of N-3-(1H-imidazol-1-yl)-propyl]-N-octyl-benz [cd] indol-2-amine, fumarate (1:2), N-[4-(1H-imidazol-1-yl)-butyl]-6-iodo-benz[cd]indol-2-amine, 1,2-dihydro-2-[[3-(1H-imidazol-1-yl)propyl]imino]-1-methyl-benz[cd]indole-6-methanol, fumarate (1:1), N-[1-(phenylmethyl)benz[cd]indol-2(1H)-ylidene]-1H-imidazole-1-butanamine, fumarate (1:2), 2-[[3-(1H-imidazol-1-yl)propyl]imino]-benz [cd]indole-1 (2H)-pentanenitrile, N,N'-[1,3-propanediylbis(benz[cd]indol-1(2H)-yl-2-ylidene)]bis-1H-Imidazole-1-propanamine, N-(1-hexylbenz[cd]indol-2(1H)-ylidene)-1H-imidazole-1-propanamine, fumarate (1:2), N-(1-hexylbenz[cd]indol-2(1H)-ylidene)-3-pyridinebutanamine, fumarate (2:3), N-[1-(3-pyridinylmethyl)benz[cd]indol-2(1H)-ylidene]-1H-imidazole-1-propanamine, N-[1-(phenylmethyl)benz[cd]indol-2(1H)-ylidene]-1H-imidazole-1-propanamine, fumarate (1:2), N-[1-(3-phenylpropyl)benz[cd]indol-2(1H)-ylidene]-1H-imidazole-1-propanamine, fumarate (1:2), N-[1-(3-phenoxypropyl)benz[cd]indol-2-(1H)-ylidene]-1H-imidazole-1-propanamine, dihydrochloride, N-[1-[(3-methoxyphenyl)methyl]benz[cd]indol-2(1H)-ylidene]-1H-imidazole-1-propanamine, N-[1-[[3-(trifluoromethyl)phenyl]methyl]benz[cd]indol-2(1H)-ylidene]-1H-imidazole-1-propanamine, N-[1-[(4-chlorophenyl)methyl]benz[cd]indol-2(1H)-ylidene]-1H-imidazole-1-propanamine, N-(1-phenylbenz[cd]indol-2(1H)-ylidene)-1H-imidazole-1-propanamine, 2-[4-(1H-imidazol-1-ylmethyl)-1-piperidinyl]-benz[cd] indole, monohydriodide (1:1 ethanol), N-[6-chloro-1-(phenyl-methyl)benz[cd]indol-2(1H)-ylidene]-1H-imidazole-1-propanamine, N-[6-chloro-1-(phenylmethyl)benz[cd]indol-2(1H)-ylidene]-3-pyridinethanamine, N-(1-(4-chlorobenzyl)-6-iodobenzo[cd]indol-2-(1H)-ylidene)-3-(1H-imidazol-1-yl)-1-propanamine, 3-(1H-imidazol-1-yl)-N-(6-iodobenzo[cd]indol-2(1H)-ylidene)-1-propanamine, N-benzyl-N-(6-iodobenzo[cd]indol-2(1H)-ylidene) amine, and (2E,6E)-N-(benzo[cd]indol-2(1H)-ylidene)-3,7,11-trimethyl- 2,6,10-dodecatrien-1-amine, or a pharmaceutically acceptable salt thereof.

9. The method of claim 1 wherein the ras-associated disease in mammals is selected from the group consisting of cancers of the pancreas, breast, lung , colon, epidermis, prostate, bladder, thyroid, myelodysplastic tumors and myeloid leukemia.

10. The method of claim 1 wherein the ras-associated disease in mammals is selected from metastasis, suppressing angiogenesis, and inducing apoptosis.

11. The method of claim 1 wherein the ras-associated proliferative disease in mammals is restenosis, neuro-fibromatosis, endometriosis, and psoriasis.

12. The method of claim 1 wherein the ras-associated disease in mammals is prenyl modifications of proteins.

* * * * *